United States Patent [19]

Puttner et al.

[11] 4,153,705
[45] May 8, 1979

[54] THIAZOLYL CINNAMIC ACID NITRILES, PESTICIDES CONTAINING THE SAME

[75] Inventors: Reinhold Puttner; Hartmut Joppien, both of Berlin, Fed. Rep. of Germany

[73] Assignee: Schering Aktiengesellschaft, Berlin, Fed. Rep. of Germany

[21] Appl. No.: 869,001

[22] Filed: Jan. 12, 1978

[30] Foreign Application Priority Data

Jan. 26, 1977 [DE] Fed. Rep. of Germany ....... 2703542

[51] Int. Cl.² ............................................ C07D 277/02
[52] U.S. Cl. ................................. 424/270; 260/302 R
[58] Field of Search ..................... 260/302 R; 424/270

[56] References Cited

U.S. PATENT DOCUMENTS 3,661,920 5/1972 Hepworth et al. ............... 260/302 R
3,840,548 10/1974 Malen et al. ..................... 260/302 R Primary Examiner—Nicholas S. Rizzo
Attorney, Agent, or Firm—Michael J. Striker

[57] ABSTRACT

Thiazolyl cinnamic acid nitriles of the formula

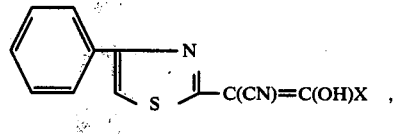

wherein X is an aromatic hydrocarbon residue which may be substituted in one or several positions by the same or different substituents selected from the group of halogen, alkyl, alkoxy, trifluoromethyl and nitro. The compounds of the invention are effective pesticides and in particular have a high insecticidal activity.

13 Claims, No Drawings

THIAZOLYL CINNAMIC ACID NITRILES, PESTICIDES CONTAINING THE SAME

BACKGROUND OF THE INVENTION

Prior art pesticides of a similar direction of activity are for instance certain phosphoric acid esters (West German Pat. No. 814,152), chlorinated hydrocarbons (West German Pat. No. 1,015,797) and carbamates (U.S. Pat. No. 2,903,478). These compounds, however, do not always exhibit a satisfactory insecticidal activity.

It is therefore an object of the present invention to provide for agents and compositions which compared with prior art agents have a superior insecticidal activity.

SUMMARY OF THE INVENTION

This object is met by compounds constituted by thiazolyl cinnamic acid nitriles of the formula

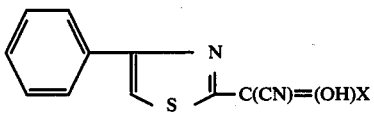

wherein X is an aromatic hydrocarbon residue which may be substituted in one or several positions by the same or different substituents selected from the group consisting of halogen, alkyl, alkoxy, trifluoromethyl and nitro.

The compounds of the invention compared with prior art compositions of similar direction of activity exhibit a superior and long-lasting insecticidal action and in addition have the significant advantage of a very low toxicity against warm blooded animals.

A further advantage of the compounds of the invention is their low toxicity towards fish and their high plant compatibility.

The compounds can be used against a large number of economically harmful pests of specific systems and orders while they do not damage important useful arthropopes.

The compounds are particularly useful against post-embryonic stages of harmful coleoptera as for instance [Sitophilus granarius, Epilachna varivestis and Leptinotarsa decemlineata, harmful Lepidopterans, e.g. Plutella maculipennis and also Hemipterans, like Dysdercus cingulatus.

In concentrations of active agents of about 0.01 to 5.0%, preferably between 0.05 and 0.5%, the compounds have a very good initial and long-lasting activity against the various pests.

COMPOSITION CONTAINING THE COMPOUNDS OF THE INVENTION

The compounds of the invention can either be used by themselves or mixed with each other or with other insecticidal agents. If desired, other plant protective agents and pesticides can be added depending on the specific purpose such as, for instance, acaricidal or fungicidal. The intensity of the action and the speed of action can be increased for instance by additives such as organic solvents, wetting agents and oils. These additives then permit a reduction of the dosage of active agents.

The compounds of the invention and their mixtures are normally used in form of compositions such as powders, dusting agents, granulates, solutions, emulsions or suspensions, all this upon addition of liquid and/or solid carrier materials or diluents and, if desired, of wetting agents, adhesion promoting agents, emulsifiers and/or dispersants.

Suitable liquid carrier materials are for instance water, aliphatic and aromatic hydrocarbons and also cyclohexanone, isophorone, dimethylsulfoxide, dimethylformamide and mineral oil fractions. Solid carrier materials are for instance mineral earths, for instance tonsil, silica gel, talcum, kaolin, attaclay, limestone, silicic acid and plant products, e.g. flours.

If surface active agents are added the following can, for instance, be used: calciumligninosulfonate, polyoxyethylene-alkylphenyl ether, naphthaline sulfonic acids and their salts, phenolsulfonic acids and their salts, formaldehyde condensation products, fatty alcohol sulfates as well as substituted benzosulfonic acids and their salts.

The amount of the active agent or agents in the various compositions can be varied widely. The compositions may for instance contain about 10 to 80% by weight of active agents, about 90 to 20% by weight of liquid or solid carrier materials and, if desired, up to 20% surface active agents upon corresponding reduction of the other liquid or solid carrier materials.

The application of the compounds can be effected in conventional form, for instance with water as carrier materials in spray amounts of about 100 to 3000 liters to about 2.5 acres. An application of the compositions is possible, in the so-called "low-volume" and "ultra-low-volume" process as well as in the form of so-called micro granulates.

The preparation of the compositions can be carried out in conventional form, for instance by mixing or grinding processes. If suitable the individual components can also be mixed only shortly for actual use as for instance in the so-called tank mixing process as it is used in actual practice.

Among the compounds of the invention those are characterized by a particularly high insecticidal activity in which the above formula X is 2-halogenophenyl, 2-$C_1$-$C_4$-alkylphenyl, 2nitrophenyl, 2-$C_1$-$C_3$-alkoxyphenyl or 2-trifluoromethylphenyl. Specific compounds with an unusual superiority of activity are 2'-chloro-3-hydroxy-2-(4-phenyl-2-thiazolyl)-cinnamic acid nitrile and the 3-hydroxy-2'-trifluoromethyl-2-(4-phenyl-2-thiazolyl)-cinnamic acid nitrile.

PROCESS OF MAKING THE COMPOUNDS

The compounds of the invention can, for instance, be made by reacting the 4-phenylthiazol-2-acetonitrile of the formula

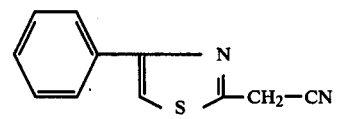

or an alkali salt thereof with a benzoylchloride of the formula

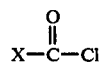

wherein X has the same meaning as in the above general formula.

Preferably the reaction is carried out by mere heating of a mixture of the components without solvent or it is carried out in an organic solvent such as for instance o-dichlorobenzene, at temperatures of 100° to 160° C., preferably between 130° and 150° C.

For large scale production it is preferred to add the benzoyl chlorides to a melt or solution of the 4-phenyl-thiazol-2-acetonitrile at a temperature between 130° and 150° C. by dropwise addition.

In case of use of an alkali salt of the 4-phenylthiazol-2-acetonitrile, for instance of a sodium or potassium salt the reaction with the benzoyl chloride can preferably be carried out in a solvent such as dimethylformamide at temperatures between 20° and 100° C., preferably at room temperature.

The following examples will further illustrate the making of the compounds.

The starting products in these cases are known products and can be made by conventional processes.

EXAMPLE 1

2'-chloro-3-hydroxy-2-(4-phenyl-2-thiazolyl)-cinnamic acid nitrile 20 g (0.1 mol) of 2-cyanomethyl-4-phenylthiazole were reacted with 17.5 g (0.1 mol) of 2-chlorobenzoyl-chloride and were slowly heated to a temperature of 140° to 150° C. The reaction mixture was maintained at this temperature for a period of 10 to 15 minutes. After cooling to 60° C. 100 ml ethanol were then added. The formed precipitate was removed by suction and washed with alcohol and water.

Yield: 26.8 g=79% of the theoretical value.
m.p.: 182° to 183° C.
Obtained: C 63.64, H 3.45, N 8.06, S 9.67, Cl 10.58%.
Theoretical: C 63.80, H 3.27, N 8.27, S 9.47, Cl 10.47%.

EXAMPLE 2

3-hydroxy-2'-nitro-2-(4-phenyl-2-thiazolyl)-cinnamic acid nitrile

A solution of 10 g (0.05 mol) of 2-cyanomethyl-4-phenylthiazole in 25 ml dimethylformamide were added dropwise at 30° C. to a suspension of 1.2 g (0.05 mol) of sodium hydride in 25 ml dimethylformamide. The mass was then subjected to stirring for 15 minutes whereupon a solution of 9.28 g (0.05 mol) of 2-nitrobenzoylchloride in 25 ml dimethylformamide was added dropwise. The reaction mixture was permitted to stand overnight and was then reacted with 750 ml water and subjected to thorough stirring. After addition of hydrochloride acid the mixture was adjusted to a faintly acid pH and was then extracted with chloroform. The chloroform phase was washed twice with water and dried on magnesium sulfate. The solvent was removed in a vacuum and the residue was digested with a small amount of methylene chloride and removed by suction.

Yield: 6.1 g=35% of the theoretical value.
m.p.: 185° to 187° C.
Obtained: C 62.32, H 3.67, N 12.32, S 8.47%. Theoretical: C 61.88, H 3.18, N 12.03, S 9.18%.

In an analogous manner the following compounds were obtained.

| Compounds | Physical constants |
|---|---|
| 3-hydroxy-2'-methyl-2-(4-phenyl-2-thiazolyl)-cinnamic acid | m.p.: 145°–146° C. |
| 2'-bromo-3-hydroxy-2-(4-phenyl-2-thiazolyl)-cinnamic acid nitrile | m.p.: 168°–169° C. |
| 2'-fluoro-3-hydroxy-2-(4-phenyl-2-thiazolyl)-cinnamic acid nitrile | m.p.: 165°–166° C. |
| 3-hydroxy-2'-iodo-2-(4-phenyl-2-thiazolyl)-cinnamic acid nitrile | m.p.: 166°–167° C. |
| 3-hydroxy-2'-methoxy-2-(4-phenyl-2-thiazolyl)-cinnamic acid nitrile | m.p.: 189°–190° C. |
| 3-hydroxy-2'-trifluoromethyl-2-(4-phenyl-2-thiazolyl)-cinnamic acid nitrile | m.p.: 197°–198° C. |
| 2'-chloro-6'-fluoro-3-hydroxy-2-(4-phenyl-2-thiazolyl)-cinnamic acid nitrile | m.p.: 221°–222° C. |
| 2'-ethyl-3-hydroxy-2-(4-phenyl-2-thiazolyl)cinnamic acid nitrile | m.p.: 186°–187° C. |

The compounds of the invention are practically insoluble in water and benzene; they have a low solubility in acetone and methylene chloride and are soluble in dimethylformamide and dimethylsulfoxide.

According to spectroscopic examination the compounds are present in enol form according to the above given formula.

Uses and Activity

The following examples will further illustrate the various uses and will show the superior activity of the compounds when compared with the prior art products.

EXAMPLE 3

The compounds of the invention were used as aqueous suspensions of the desired concentration indicated below. The comparison compounds were likewise diluted with water and used as suspensions or emulsions in the indicated concentrations.

The preparations were adjusted to the required dosage in Petri dishes and were applied by spraying in aqueous spray amounts of 4 mg/cm$^2$. The deposits formed by the spraying were permitted to age in air for either 10 days, 17 days or 28 days. There were then exposed to them for 4 days about 100 adult grain beetles (*Sitophilus granarius*) per test in closed Petri dishes. The criterion for the activity was the mortality of the beetles expressed in percentage after an exposure of 4 days. The results obtained appear from the following Table 1.

TABLE 1

| Compounds of the Invention | Concentration in % of active agent | Mortality in % Agent aged after spraying for: | | |
|---|---|---|---|---|
| | | 10 days | 17 days | 28 days |
| 2'-chloro-3-hydroxy-2-(4-phenyl-2-thiazolyl)-cinnamic acid nitrile | 0.02 | 100 | 100 | 100 |
| | 0.01 | 100 | 100 | 91 |
| | 0.005 | 100 | 97 | 76 |
| 2'-bromo-3-hydroxy-2-(4-phenyl-2-thiazolyl)-cinnamic acid nitrile | 0.02 | 100 | 100 | 28 |
| | 0.01 | 91 | 90 | 10 |
| | 0.005 | 82 | 86 | 1 |
| Comparison compounds | | | | |

TABLE 1-continued

| | | | | |
|---|---|---|---|---|
| 0.0-dimethyl-0-(p-nitrophenyl) | 0.02 | 100 | 100 | 0 |
| thiono-phosphoric acid ester | 0.01 | 100 | 52 | 0 |
| West German Patent 814 152 | 0.005 | 49 | 6 | 0 |
| 6,7, 8,9,10-hexachloro-1,5,5a, | 0.02 | 73 | 42 | 0 |
| 6,9, 9a-hexahydro-6,9-methano- | 0.01 | 74 | 26 | 0 |
| 2,4,3-benzodioxathiepin-3-oxide | 0.005 | 68 | 18 | 0 |
| (West German Patent 1,015,797) | | | | |

EXAMPLE 4

The compounds of the invention were applied as aqueous suspensions in the concentrations indicated below. The comparison compounds were likewise diluted with water and used as suspensions or emulsions in the indicated concentrations.

The active agents prepared in this form were applied to cauliflower leaves in plastic Petri dishes. The application was by spraying in dosages of 4 mg of aqueous spray amount per cm$^2$. After drying of the spray deposits there were placed into each Petri dish 10 juvenile larvae of the cabbage roach (*Plutella maculippenis*). The insects were exposed for 3 days in the closed Petri dishes to the thus pretreated feed material.

Criterion for the activity was the mortality of the larvae in percentages after 3 days.

The following Table II shows the results obtained.

TABLE II

| Compounds of the Invention | Concentration in % of active agent | Mortality in % |
|---|---|---|
| 2'-chloro-3-hydroxy-2-(4-phenyl-2-thiazolyl)-cinnamic acid nitrile | 0.008 | 100 |
| 2'-nitro-3-hydroxy-2-(4-phenyl-2-thiazolyl)-cinnamic acid nitrile | 0.008 | 100 |
| Companion compounds | | |
| 1-naphthyl-methylcarbamate (U.S. Pat. No. 2,903,478) | 0.008 | 70 |
| 0,0-dimethyl-0-(p-nitro-phenyl)-thiono-phosphoric acid ester (West German Patent 814,152) | 0.008 | 75 |

EXAMPLE 5

The compounds of the invention were applied as aqueous suspensions in the concentrations indicated below. The comparison compound was likewise used as an aqueous emulsion of the indicated concentration.

These active agents were sprayed dropwise on bush-beans (*Phaseolus vulgaris*) in the primary leaf stage. 11 days after application 5 plants each were placed in water-filled glass vessels after removal of the secondary leaves and roots. There were then added in glass cylinders 5 larvae each of the (LIII) Mexican bean bug (*Epilachna varivestis*).

Criterium for the activity was the mortality of the larvae expressed in percentages after a test time of 7 days. The results obtained appear from the following Table III.

TABLE III

| Compounds of the Invention | Concentration in % of active agent | Mortality in % |
|---|---|---|
| 2'-chloro-3-hydroxy-2-(4-phenyl-2-thiazolyl)-cinnamic acid nitrile | 0.04 | 100 |
| 2'-bromo-3-hydroxy-2-(4-phenyl-2-thiazolyl)-cinnamic acid nitrile | 0.04 | 87 |

TABLE III-continued

| Comparison compound | | |
|---|---|---|
| 0,0-dimethyl-0-(p-nitro-phenyl)-thiono-phosphoric acid ester (West German Patent 814,152) | 0.04 | 20 |

EXAMPLE 6

This test was carried out with infested specially marked potato plants grown in open air on test lots. The plants had been infested with larvae of the potato beetle (*Leptinotarsa decemlineata*) of which the number had been determined prior to the treatment and then again on the first, third and seventh day after treatment. The activity of the compounds was determined by the formula of Schneider-Orelli.

The amounts used corresponded to 200 g of active agent and in case of the comparison compound to 225 g of active agent, in both cases applied in 600 liter of water per about 2.5 acres.

The results appear from the following Table IV.

TABLE IV

| | activity in % | | |
|---|---|---|---|
| Compound of the Invention | 1 day | 3 days after spraying | 7 days |
| 2'-chloro-3-hydroxy-2-(4-phenyl-2-thiazolyl)-cinnamic acid nitrile | 78 | 92 | 94 |
| Comparison compound | | | |
| 6,7,8,9,10,10-hexachloro-1,5,5a, 6,9,9a-hexahydro-6.9-methano-2,4,3-benzodioxathiepin-3-oxide (West German Patent 1,015,797) | 71 | 82 | 75 |

EXAMPLE 7

Compounds of the invention were applied as aqueous suspensions at the concentrations indicated below.

These preparations were applied by spraying cauliflower leaves in plastic Petri dishes with amounts of 4 mg of spray liquid per cm$^2$. After drying of the sprayed amounts 10 larvae of the cabbage roach (*Plutella maculippenis*) were placed in each Petri dish and were exposed for two days in the closed dishes to the pretreated feed.

Criterion for the activity was the mortality of the larvae in percentages after two days.

The following Table V shows the results obtained.

TABLE V

| Compounds of the invention | Concentration in % | Mortality in % |
|---|---|---|
| 3-hydroxy-2'-nitro-2-(4-phenyl-2-thiazolyl)-cinnamic acid nitrile | 0.04 | 100 |
| 3-hydroxy-2'-methyl-2-(4-phenyl-2-thiazolyl)-cinnamic acid nitrile | 0.04 | 100 |
| 2'-bromo-3-hydroxy-2-(4-phenyl-2-thiazolyl)-cinnamic acid nitrile | 0.04 | 100 |

TABLE V-continued

| Compounds of the invention | Concentration in % | Mortality in % |
|---|---|---|
| 2'-fluoro-3-hydroxy-2-(4-phenyl-2-thiazolyl)-cinnamic acid nitrile | 0.04 | 100 |
| 3-hydroxy-2'-iodo-2-(4-phenyl-2-thiazolyl)-cinnamic acid nitrile | 0.04 | 95 |
| 3-hydroxy-2'-methoxy-2-(4-phenyl-2-thiazolyl)-cinnamic acid nitrile | 0.04 | 100 |
| 2'-chloro-6'-fluoro-3-hydroxy-2-(4-phenyl-2-thiazolyl)-cinnamic acid nitrile | 0.04 | 100 |
| 2'-ethyl-3-hydroxy-2-(4-phenyl-2-thiazolyl)-cinnamic acid nitrile | 0.04 | 80 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Thiazolyl cinnamic acid nitrile of the formula

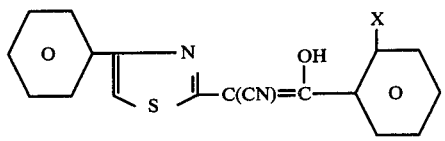

wherein X is a residue selected from the group consisting of alkyl of up to four carbons, alkoxy of up to three carbons, trifluoromethyl, nitro, and halogen selected from the group consisting of chloro, bromo, fluoro and iodo.

2. A pesticide composition with insecticidal activity comprising about 10 to 80% by weight of thiazolyl cinnamic acid nitrile of the formula

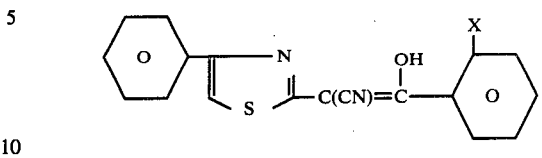

wherein X is selected from the group consisting of alkyl of up to four carbons, alkoxy of up to three carbons, trifluoromethyl, nitro, and halogen selected from the group consisting of chloro, bromo, fluoro and iodo, and about 90 to 20% by weight of liquid or solid carrier material.

3. The compound of claim 1 which is 2'-chloro-3-hydroxy-2-(4-phenyl-2-thiazolyl)-cinnamic acid nitrile.

4. The compound of claim 1 which is 3-hydroxy-2'-nitro-2-(4-phenyl-2-thiazolyl)-cinnamic acid nitrile.

5. The compound of claim 1 which is 3-hydroxy-2'-methyl-2-(4-phenyl-2-thiazolyl)-cinnamic acid nitrile.

6. The compound of claim 1 which is 2'-bromo-3-hydroxy-2-(4-phenyl-2-thiazolyl)-cinnamic acid nitrile.

7. The compound of claim 1 which is 2'-fluoro-3-hydroxy-2-(4-phenyl-2-thiazolyl)-cinnamic acid nitrile.

8. The compound of claim 1 which is 3-hydroxy-2'-iodo-2-(4-phenyl-2-thiazolyl)-cinnamic acid nitrile.

9. The compound of claim 1 which is 3-hydroxy-2'-methoxy-2-(4-phenyl-2-thiazolyl)-cinnamic acid nitrile.

10. The compound of claim 1 which is 3-hydroxy-2'-trifluoromethyl-2-(4-phenyl-2-thiazolyl)-cinnamic acid nitrile.

11. The compound of claim 1 which is 2'-chloro-6'-fluoro-3-hydroxy-2-(4-phenyl-2-thiazolyl)-cinnamic acid nitrile.

12. The compound of claim 1 which is 2'-ethyl-3-hydroxy-2-(4-phenyl-2-thiazolyl)-cinnamic acid nitrile.

13. The pesticide composition of claim 2 which contains 20% by weight of said thiazolyl cinnamic acid nitrile and 80% by weight of said liquid or solid carrier materials.

* * * * *